United States Patent
Le Gargasson et al.

(10) Patent No.: US 6,588,900 B1
(45) Date of Patent: Jul. 8, 2003

(54) HIGH RESOLUTION DEVICE FOR OBSERVING A BODY

(75) Inventors: Jean-François Le Gargasson, Villiers S/Marne (FR); Pierre Lena, Paris (FR); Claude Boccara, Paris (FR); Arnaud Dubois, Les Ulis (FR)

(73) Assignee: Universite Paris 7-Denis Diderot, Paris (FR)

( * ) Notice: Subject to any disclaimer, the term of this patent is extended or adjusted under 35 U.S.C. 154(b) by 0 days.

(21) Appl. No.: 09/958,106
(22) PCT Filed: Mar. 31, 2000
(86) PCT No.: PCT/FR00/00823
§ 371 (c)(1), (2), (4) Date: Jan. 23, 2002
(87) PCT Pub. No.: WO00/59368
PCT Pub. Date: Oct. 12, 2000

(30) Foreign Application Priority Data

Apr. 1, 1999 (FR) .............................. 99 04086

(51) Int. Cl.⁷ ................................................ A61B 3/00
(52) U.S. Cl. ....................... 351/200; 351/212; 351/247
(58) Field of Search ................................. 351/200, 212, 351/247, 221, 246, 205, 211, 219

(56) References Cited

U.S. PATENT DOCUMENTS 5,777,719 A * 7/1998 Williams et al. ............. 351/212
5,949,521 A * 9/1999 Williams et al. ............. 351/246
6,271,914 B1 * 8/2001 Frey et al. .................... 356/124

\* cited by examiner

*Primary Examiner*—George Manuel
*Assistant Examiner*—Runa Shah Qaderi
(74) *Attorney, Agent, or Firm*—Blakely Sokoloff Taylor & Zafman

(57) ABSTRACT

The invention concerns a device for observing a body, in particular a viewer, comprising means for illuminating (12) the body (5), means for sampling (400, 450, 500, 700) light coming from an illuminated site (01) of the body and compensating means (20) for measuring a deformation of the wave front of a beam coming from a point of the body (5) and for applying to the light sampled by the sampling means (400, 450, 500, 700) a correction calculated on the basis of said measured deformation. The invention is characterised in that the sampling means and the compensating means are arranged such that, for each point of the body used for calculating the correction, the sampling means sample the light on a selected zone of the body near enough to said calculation point for the deformation of the wave front of the light coming from any point of that zone should be the same as that coming from the point of calculation more or less within a wavelength fraction, and the device includes means (400, 450, 500, 700) for automatically changing the point of the body (5) used for the calculation of correction and for changing synchronously the associated sampling zone, such that the device scans the observed body by way of a series of such successive zones for each of which the deformation of the wave front derived from any point in the zone is identical, more or less within a wavelength fraction, to the deformation of the wave front derived from the associated point of calculation.

14 Claims, 3 Drawing Sheets

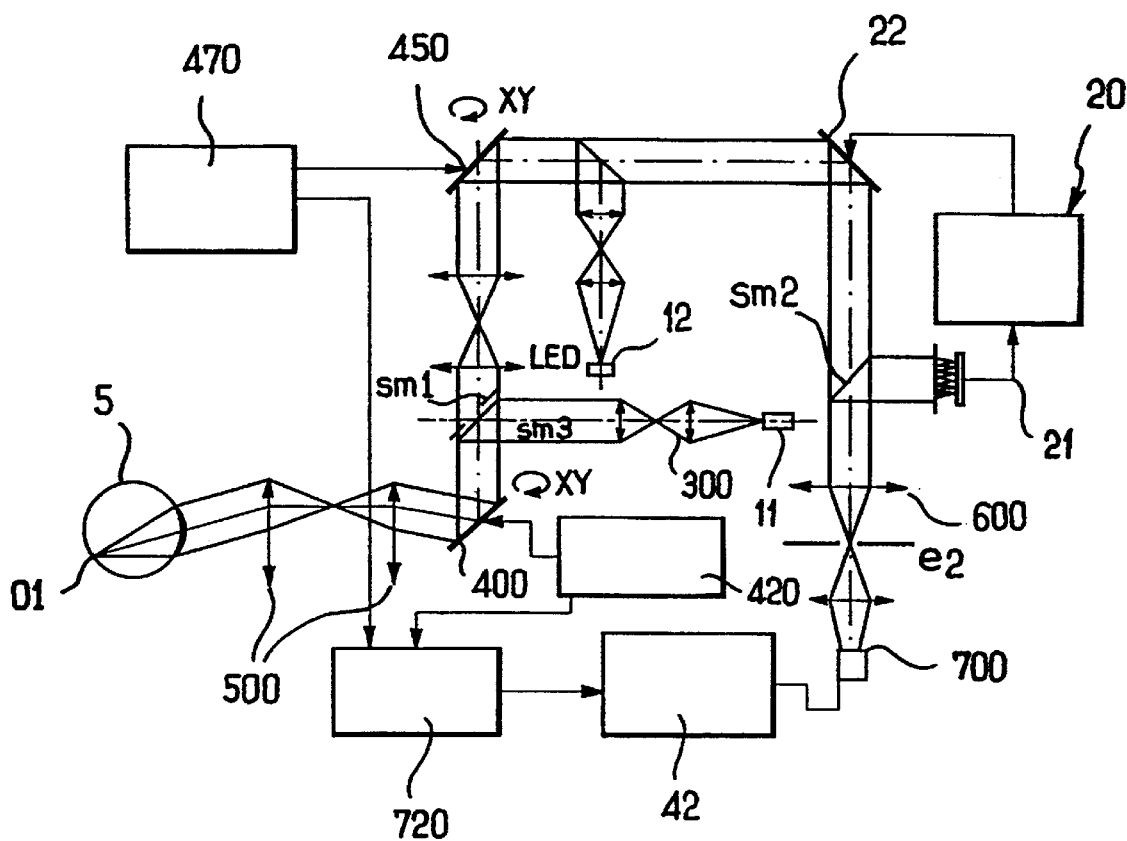
FIG_2

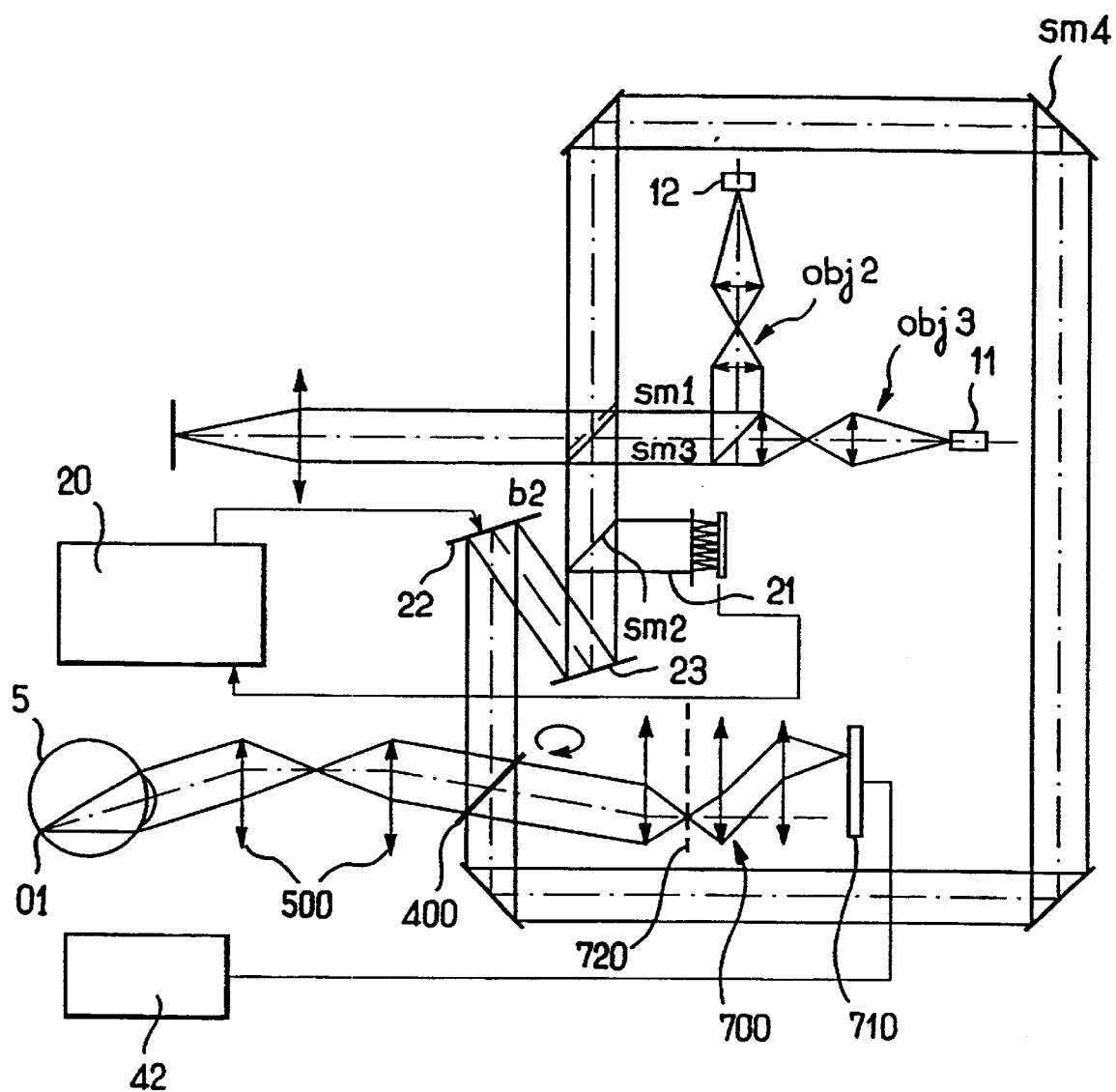
FIG_3

HIGH RESOLUTION DEVICE FOR OBSERVING A BODY

The invention relates to devices for observing bodies, for example living bodies or manufactured articles.

It relates especially to devices for observing an eye.

Many devices are known for observing an eye, such as biomicroscopes, ophthalmoscopes or retinographic devices. They make use of various types of examinations, such as direct anatomical observations or scanning by means of dyes, such as fluorescein, indocyanin green, rose bengal or acridine orange.

With certain recent experimental apparatuses, functional scanning is also possible, such as the study of attachments or the projecting of tests intended for the recording of electrical activity of visual pathways. In this case, an image is formed directly on the retin a by means of modulation of an illumination beam.

The most conventional apparatuses are based on overall illumination with a field of 5° to 60° in polychromatic or monochromatic light.

In general, these apparatuses need to separate the illumination and observation pupils according to the so-called Gullstrand principle.

Retinographic devices use a photographic sensitive surface. They require much higher levels of retinal illumination than those required for ophthalmoscopic observation directly via the observer's retina. Their level of performance is essentially defined by the optical resolution of the system.

More recently, sensitive surfaces have appeared which allow videoscopic recordings at wavelengths visible or nonvisible to the human eye. The resolution of these apparatuses is therefore subject, in addition to the optical limitations, to the limitations of the electronic acquisition.

In the field of the scanning of the cornea and the lens, illumination systems are known whose illumination source has the form of a circle or of a slit of variable width and whose optical image is focused onto the plane of observation.

In such devices, an observation system consisting of a monocular or binocular magnifying system fastened to the illumination device is used. The image of tissues may be observed either directly or via an additional lens placed close to the eye. These apparatuses meet the provisions of a pupil separation principle, called the Gullstrand principle.

More recently, corneal and/or lens microscopy apparatuses have been described. These apparatuses are very similar to those in conventional microscopy. These apparatuses use the fact that the anterior media of the eye make it possible to work with very wide beam angles, using what is called the immersion technique.

Recently, a novel technique called confocal microscopy has also been proposed for displaying the cornea. The confocal technique has the advantage of selecting a plane of optical section having a certain thickness in Z. Apparatuses making use of this technique therefore have tomographic properties, that is to say they make it possible to isolate a plane of observation in a scattering medium. Videoscopic techniques allow acquisition in real time of a large number of optical sections in successive planes.

In the field of retinal scanning, it has also been proposed to use a technique based on principles different from the above principles defined by Helmholtz in the middle of the nineteenth century.

U.S. Pat. No. 4,213,678 by Pomerantzeff and Webb has thus proposed illuminating a small area scanning the field of view. This patent teaches the use of optomechanical scanning for deflecting, in two dimensions, a light beam having a diameter of less than that of the eye's pupil. The apparatus collects, at full pupil, the flux reflected and/or scattered by the ocular tissues. This apparatus is consistent with the Gullstrand principle, thereby limiting the resolution by using a reduced illumination pupil. This document proposes to remedy the presence of reflections by using polarized light.

In patent EP 145 563, Cohen Sabban, Roussel & Simon propose to make the flux reflected and/or scattered by the ocular tissues follow the same path as the illumination flux. This reflected flux follows the optical deflection path and thus becomes immobile. The authors call this action beam stabilization. This optical device permits filtration of the return beam coming from the eye, using spatial filtration elements in a plane conjugate with the source and with the optical tissues observed. This description corresponds to the use of a confocal device. This optical device makes it possible to eliminate reflections without using the Gullstrand pupil separation principle.

The use of the same pupil for the illumination and observation paths gives better resolution than the device of document U.S. Pat. No. 4,213,678. The use of confocal filtering makes it possible to increase the contrast by eliminating the flux scattered by the planes superjacent and subjacent to the plane observed.

In 1987, Webb and Hughes, in patent EP 223 356, adopt the principle of stabilizing the illumination and observation beam, but they retain the separation of the pupils in the stabilized return beam. This device is more effective than the previous one with regard to the elimination of pupillary reflections, but it still has the drawback of collected flux limitation.

The use of spatial filtering devices in the stabilized return path makes it possible to obtain images whose depth of field is defined by the diameter of the filtration pupil. This tomographic aspect permits the construction of three-dimensional images of the tissues studied. However, the resolution obtained is tied to the geometrical aberrations and to the fluctuations in the transparent media. It remains limited to 30 $\mu$m over the XY area of the retina and to 300 $\mu$m in the case of the depth Z of the retinal tissue.

In the field of corneal and retinal scanning, Izaat et al have proposed scanning by interferometry with a device of the Michelson interferometer type.

The latter uses an illumination source of low spatio-temporal coherence. The depthwise Z resolution is determined by the coherence characteristics of the source. The use of a light-emitting diode allows a 15 $\mu$m Z resolution in the eye and 20 $\mu$m Z resolution at the cornea.

The image of an optical section is obtained, in Z retinal depth, by a succession of interference patterns produced between the flux coming from the tissues to be scanned and a reference flux coming from a mirror placed in what is called the reference arm. Each position of the reference mirror provides an interference system which will be scanned and will provide the information for a pixel in Z.

Scanning along a line is obtained by optomechanical scanning, making it possible to scan a new position when scanning in Z for a previous position has been completed. The XYZ resolution is of the order of 20 $\mu$m under the best conditions.

This device is sensitive to the movements of the eye, since the acquisition time is relatively long compared with the bandwidths of the ocular movements. Correction algorithms are able only partially to compensate for this shortcoming. This device gives an image of various relative positions and does not make it possible to give a faithful and absolute topographic image. The actual resolution obtained is of the order of 100 μm in X or Y and 50 μm in Z.

In the field of adaptive optics, it has been proposed in patent U.S. Pat. No. 5,777,719 to insert a wavefront compensation device using a deformable mirror in a conventional retinographic system. One point on the surface is illuminated by a superluminescent diode which makes it possible to measure the distortions of the wavefront and to calculate the compensation which must be applied by the deformable mirror. This compensation is carried out over a complete image of the fundus of the eye, and acquired by a CCD camera. This technique makes is possible to obtain an XY resolution of 2 μm, which is unsatisfactory.

In addition, this device does not make it possible to extract a useful signal corresponding to a chosen optical plane of the tissue studied by avoiding all reflections and backscattering coming from the subjacent and superjacent planes.

An overall objective of the invention is to provide a device for observing a body, such as the body of a living person or such as a manufactured article, having a particularly improved image resolution over those provided by the existing devices.

This objective is achieved according to the invention by virtue of a device for observing a body, especially an eye, comprising means for illuminating the body, means for sampling the light coming from an illuminated region of the body and compensation means capable of measuring a wavefront distortion of a beam coming from a point on the body and in applying, to the light sampled by the sampling means, a correction calculated from this measured distortion, characterized in that the sampling means and the compensation means are arranged so that, for each point on the body used for a correction calculation, the sampling means sample the light over a chosen region of the body sufficiently close to said point of calculation for the wavefront distortion of the light coming from any point in this region is the same as that coming from the point of calculation to within a fraction of a wavelength, and in that the device includes means for automatically changing the point on the body used for the correction calculation and for changing, synchronously, the associated sampling region in such a way that the device scans the observed body in the form of a series of such successive regions for each of which the distortion of the wavefront emanating from any point in the region is identical, to within a fraction of a wavelength, to the distortion of the wavefront emanating from an associated point of calculation.

Further features, objectives and advantages of the invention will become apparent on reading the detailed description which follows, given with reference to the appended figures in which:

FIG. 2 is a detailed functional representation of an ophthalmoscope according to a first embodiment of the invention, using a confocal filtering technique to extract the signals coming from the eye;

FIG. 3 is a detailed functional representation of an ophthalmoscope according to a second embodiment of the invention, using an interferometric technique to extract the signal coming from the eye.

Figure 1:
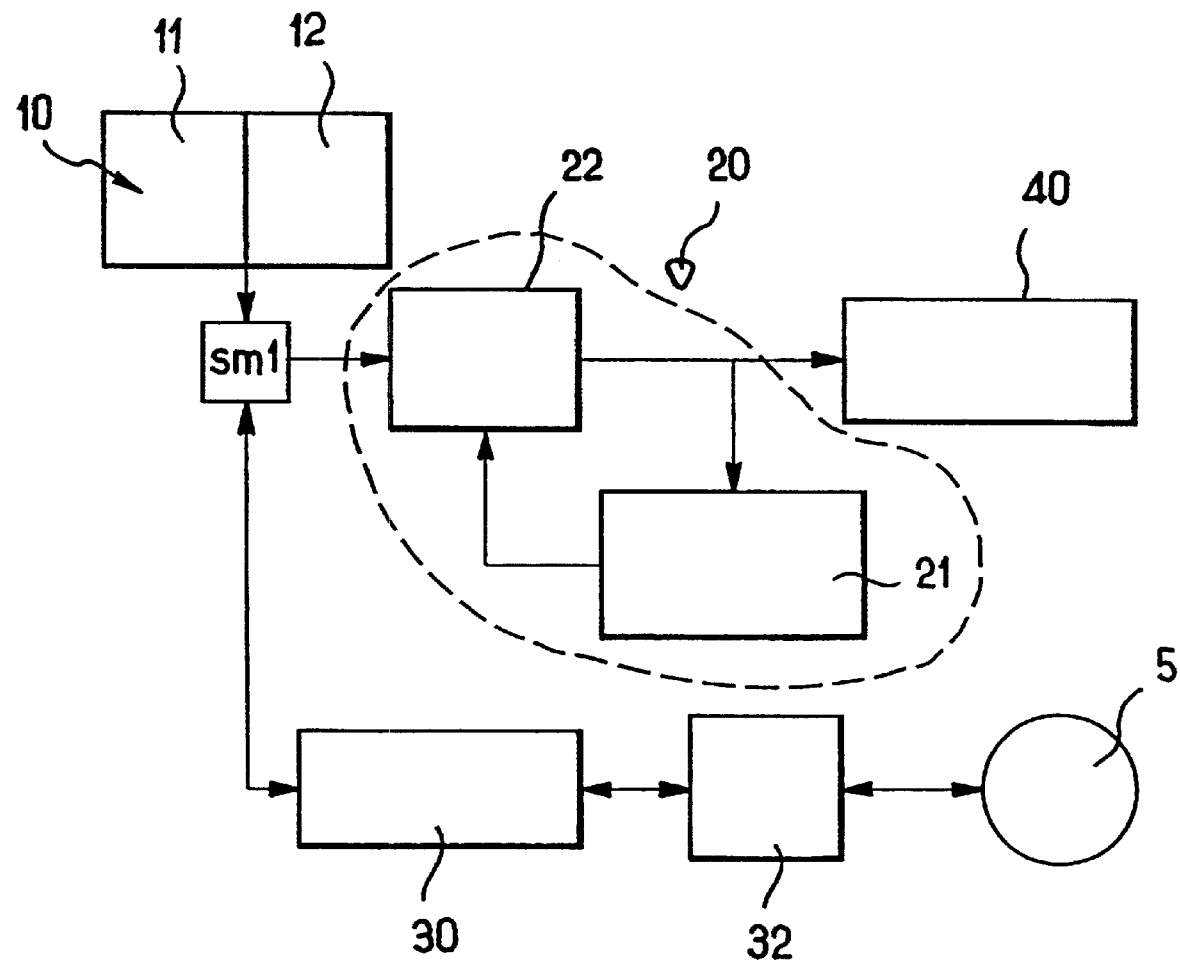
FIG. 1 is a diagram in the form of functional blocks of an ophthalmoscope according to the invention.

In the description which follows, the term "isoplanar surface or microsurface" refers to an observation surface of approximately planar shape, which fulfills the condition that the wavefronts coming from any point belonging to it are identical to within a fraction of a wavelength. Such a surface may, for example, consist physically of one face of a body or may also consist of a plane of section through a scattering medium.

"Fraction of a wavelength" is understood to mean a deviation of less than one wavelength.

In the document "Objective measurement of wave aberrations of the human eye with the use of a Hartman-Schack wavefront sensor" by V. Liang et al, Journal of the Optical Society of America, Vol. 11, No. 7, July 1994, a method of measuring wavefront distortions has been proposed which can be used within the context of the invention to identify the wavefront distortion and thus the shape identity or otherwise between two wavefront distortions. This measurement method, which is explained in detail in said document in the case of a beam coming from the human eye, is applicable to the determination of the wavefront distortion emanating from any observed body.

More specifically, in the devices that will be described hereafter, the criterion of isoplanarity of a microsurface will be defined by the fact that the wavefronts emanating from any point on this surface are identical within approximately a quarter of a wavelength.

The isoplanar microsurfaces are determined by a prior study of the wavefront distortions over a defined surface. When the wavefront distortions depart from this criterion, the scanned surface is not isoplanar. It then becomes necessary according to the invention to reduce the area of the surface until it becomes isoplanar again.

This iterative process of identifying an isoplanar surface can be carried out at the stage of defining the parameters of the device of the invention so as to define a mean extent of the isoplanar surfaces, or be carried out by an automatic module integrated into a device according to the invention, the role of which, for each chosen position on a surface, is to determine its extent so that it is isoplanar.

The structure of FIG. 1 comprises four main members, namely a light source unit 10, an servocontrolled optics device 20, a stepper scanning device 30 and an image capture and construction device 40.

Preferably, the source unit 10 comprises two particular sources; a source 11 intended for measuring the wavefront distortions of the isoplanar surfaces and a source 12 intended for constructing an image of an isoplanar surface.

The intensity of the sources 11 and 12 are chosen to be compatible with the safety rules regarding biological tissues (AFNOR C 43 801, 1992 and ANSI Z136.1, 1993 standards). The sources may be modulated by control electronics so as to use only the wavefront measurement source 11 during a wavefront measurement phase and the source 12 only during a separate image construction phase.

The servocontrolled optics device 20 is placed in the circuit for the light flux backscattered by the ocular tissue 5. It comprises a wavefront distortion measurement device 21 and a wavefront correction or compensation device 22.

The compensation device 22 is placed in front of the measurement device 21 in the path of the flux coming from the eye (or from another body, such as a manufactured article). It constitutes with the latter a feedback-loop servocontrolled system.

The device 21 consists, for example, of a wavefront measurement system of the Hartmann & Shack type, which splits the beam into a large number of subpupils, or else of a wavefront curvature scanning device. This device is preferably located in an optical plane conjugate with the subject's pupil, but it may be placed in any other plane deemed to be optimal. This optical system measures the aberrations, especially the geometrical aberrations, of dioptric interfaces and the temporo-spatial fluctuations of the indices of the transparent media, together with the aberrations generated by a device using wide-aperture optical systems.

The device 22 may consist of a deformable mirror having a certain number of actuators capable of deforming it. It compensates for the spatio-temporal differences in the optical path which constitute the distortion of the wavefront. Provision is also made to use any equivalent device, such as a set of independent micromirrors or liquid crystals. This device thus compensates for optical defects arising from the observed object or from the observation system itself.

The mirror 22, represented here as deflecting the light flux through 90°, is advantageously placed so as to reflect the flux through an angle of less than 90° with respect to the incoming flux on the mirror.

Under such control loop conditions, the resolution is determined both by the diffraction limit and by the quality of this adaptive control system.

The purpose of the stepper scanning device 30 is to change the microsurface observed. It directs the optical flux emitted by the source 12 so as to scan in succession a series of microsurfaces. To do this, it comprises, for example, optomechanical deflectors controlled by stepper motors.

The step is determined by the extent of the isoplanar surfaces that it is desired to scan. It may be fixed or be set by the user depending on the quality of the image and the field that it is desired to observe. To observe large fields, the entire surface of which does not satisfy the isoplanarity conditions defined above, the step is chosen so that the parts scanned in succession meet the isoplanarity characteristics.

In a preferred embodiment, the illumination flux and the flux backscattered by the tissues follow the same path, so that the return beam is stabilized by the deflection device 30.

A splitter SM1 is optically linked between the three modules, namely the source unit 10, the servocontrolled optics module 20 and the scanning module 30. The purpose of this splitter SM1 is to transmit the flux emitted by the sources 11 and 12 to the scanning device 30 and to transmit the return flux coming from the scanning module 30 to the servocontrolled optics device 20. The adaptive optics part 20 therefore receives a stabilized signal.

The image capture and construction device 40 is an optoelectronic receiver comprising an electronic and data processing unit provided with a clock unit which generates the sequence of all the events and amplifies and processes all the signals coming from sensors and from possible elements for modulating the illumination flux or from possible dynamic filtering control elements which will be described below. It also carries out the processing of information in order to display and store the images obtained.

The devices described below will use the elements of the device in FIG. 1, these common elements bearing the same reference numbers.

The device of FIG. 2 will now be described more specifically.

The wavefront measurement is carried out in this device by forming as small an illumination spot as possible in the scanned tissue. To do this, the light emitted by a superluminescent diode 11 enters the eye 5 after having passed through a lens 300, having been reflected off a splitter mirror SM1 and then off a moving mirror 400 for changing the microsurface and after having passed through a pair of lenses 500, also forming the optical entrance of the device.

The wavefront analyzer 21 is located in an optical plane conjugate with that of the subject's pupil. To reach this analyzer 21, the backscattered flux passes through the pair of lenses 500, is reflected by the moving mirror 400, passes through the splitter mirror SM1 and is reflected by a second moving mirror 450.

The illumination source 12 is placed directly upstream of this mirror 450, the light emitted by the source 12 being directed onto the moving mirror 450 by a semitransparent mirror at 45°.

The optical system is designed so that the illumination flux emitted by the diode 12 forms a light focal spot on the retina. As will be described below, only the rays backscattered by this focal spot will be sampled. The device therefore uses the confocal scanning technique.

The mirror 450 is thus designed to scan the interior of the microsurface corresponding to the chosen position of the mirror 400. The entire isoplanar surface corresponding to each position of the mirror 400 is scanned by the mirror 450.

The purpose of the diode 11 is to illuminate a spot on the retina of the eye 5, so that the compensation device 20 derives, by calculation on the flux backscattered by this point, a wavefront correction to be applied to the optical signals passing through it.

Thus, for each correction calculation, that is to say for each point illuminated by the diode 11, a new compensation is applied to all of the light flux picked up from the eye 5, that is to say the light flux coming from the diode 12, forming a light focal spot on the eye, this flux being backscattered by the tissues, and directly joining the optical entrance 500 of the system from the focal point of the light rays.

According to the invention, associated with each new position of the mirror 400 is a new compensation calculation and a new correction by the mirror 22. Since the extent of the microsurface scanned by the mirror 450 for a given position of the mirror 400 is chosen so that this surface is isoplanar, the correction applied by the module 20 remains constant throughout the scanning of this surface. All the flux picked up from this surface is therefore subjected to this correction calculated beforehand, which correction is suitable for this chosen surface because of the fact that it exhibits isoplanarity. When the isoplanar surface is changed, that is to say when the mirror 400 moves to a new position, a new compensation calculation is carried out on the basis of the illumination by the diode 11 of a point on this new isoplanar surface.

The light sampling means, that is to say especially the mirrors 400 and 450 and the capture device 400, and the sampling means, that is to say especially the compensation module 20 and the mirror 400, are therefore synchronized so that a new point of compensation calculation is used in an optimal manner by the deflectors 400 and 450 which exploit this correction for the entire sampling extent suitable for this correction. Thus the maximum benefit is drawn from each new correction. To illuminate a wavefront distortion measurement point lying in the sampling surface, the flux emitted by the diode 11 is directed onto the mirror 400 via a semitransparent mirror SM1, parallel to a direction of the illumination rays corresponding to a mean position of the mirror 450.

The mirror 400 is controlled by a module 420 synchronized to a sensor 700 by a synchronization module 720. The mirror 450 itself is also controlled by a module 470 synchronized to the mirror 400 and to the sensor 700 by means of the module 720.

According to the embodiment of the invention described here, the extent of the isoplanar surfaces is determined in advance. However, provision is made according to the invention to provide the device with a module capable, for each new position of the mirror 400, of determining the extent of the sampling surface corresponding to this position so that the latter verifies the isoplanarity criterion.

The isoplanar microsurface studied 01 is illuminated point after point by the light-emitting diode 12 focused onto the tissue plane studied. The illumination spot has the smallest possible diameter.

The additional scanning device 450 lies in an optical plane conjugate with the subject's pupil. Specific scanning intended to scan the actual microsurface is therefore carried out.

In this preferred embodiment, the illumination flux and the flux backscattered by the tissues follow the same path, so that the return beam is stabilized by the deflection device consisting of the two mirrors 400 and 450. This return flux is not collected in the pupillary plane as in the document U.S. Pat. No. 4,213,678.

The stabilized and corrected flux is transmitted to a confocal filtering device or spatial filtering device, placed in the plane conjugate with the retina, in front of the detector intended to image the retina.

This confocal spatial filtering unit consists of a filtering hole with the diameter of a diffraction spot. It lies, by virtue of a lens 600, in a plane conjugate with the source 12 and with the scanned retinal tissue 5.

The image construction device placed downstream of this confocal filter consists of a detector 700 of the photomultiplier or avalanche photodiode or CCD type. It therefore detects the backscattered flux which has come from the tissues 5 studied and has passed through the elements 500, 400, SM1, 450, 20 and 600. The flux detected by the sensor 700 is amplified and then processed by the electronic unit 42 in order to display the tissue image.

The sensor 700 here is a single, non-matrix, sensor. The device therefore includes an electronic system for the temporo-spatial conversion of the information which makes it possible, based on a single sensor, to fill in a matrix of values corresponding to the measurements carried out at each point making up the microsurface.

The temporal information in the backscattered flux is converted into spatial information by this electronic system filling in a matrix synchronously and homothetically with the movements of the scanning systems 400 and 450.

The confocal filtration device makes it possible to work with a wide or a narrow spectral range. Fluorescence images are also possible.

Under the conditions described above, the resolution is 2 $\mu$m in the plane of the retinal surface XY and 10 $\mu$m in the retinal depth Z. A major advantage of this device is that it allows fluorescence studies to be carried out. Such a device makes it possible to produce images with a wide field of more than 10°.

In a second embodiment of the invention, images are created from interference between a flux backscattered by the observed tissue plane and a flux in a reference arm which travels the same optical distance as the backscattered flux to within the spatio-temporal coherence length.

The wavefront distortion correction is made on the stabilized flux before making the addition coherent with the signal of the reference arm.

The wavefront measurement is here again carried out by forming as small an illumination spot as possible in the scanned tissue. This is obtained by a superluminescent diode 11 and an optical device capable of generating a point where the light rays are focused in the observed tissue.

The illumination source 12 used for constructing an image has a low spatio-temporal coherence in order to obtain a resolution in Z of a few micrometers. This is, for example, a light-emitting diode. The resolution in Z depends on the temporal coherence of the illumination source and also on the aperture of the optical system.

The path traveled by the light beams in the reference arm and in the observation arm must therefore be strictly identical.

To achieve this objective, an optomechanical device able to simulate as close as possible the optical behavior of the eye is placed in the reference arm. When the spatio-temporal coherence conditions are fulfilled for both branches, interference patterns form which, after suitable data processing, (synchronous detection and calculations) make it possible to obtain the image of the tissue plane studied.

The illumination flux delivered by the diode 12 is directed onto the retina via a moving mirror 400 capable of directing this flux onto a chosen isoplanar microsurface O1.

The flux backscattered by the microsurface studied O1 is directed toward a combining plate SM1.

To reach this combining plate SM1, the backscattered flux follows, in the reverse direction, part of the path of the illumination flux. In particular, it passes through a moving microsurface-changing mirror 400, a deformable wavefront-compensating mirror 22, a deflection mirror 23 and a wavefront distortion measurement module 21 coupled to the mirror 22, and then reaches the combining plate SM1.

The reference flux is emitted by the diode 11, deflected by the semitransparent splitter mirror SM1, and then follows the same path as the backscattered flux.

The combined flux output by SM1 is directed onto a second face of the mirror 400, which deflects this flux corresponding to an entire isoplanar surface onto an image construction device.

The combiner SM1 therefore combines the flux coming from the reference arm, consisting of the elements described above and labeled 11, SM1, SM2, 23, 22 and SM1, with the backscattered tissue flux coming from the elements described above and labeled 5, 400, 22, 23, SM2, SM1.

An optical device downstream of the diodes 11 and 12 and upstream of the splitter SM1 makes it possible to combine the flux output directly by the diode 11 with the flux output directly by the diode 12 and to regulate the power of the beam emitted by each of them. To do this, two optical systems obj2 and obj3 are placed in front of the diodes and make it possible to choose the position of the plane studied.

The interference images are formed in the plane of a sensor 710 and correspond, at each position of the mirror 400, to the entire isoplanar surface which it is desired to display.

The source 12, intended for tissue imaging, forms an illumination area on the retina of an eye 5 which is equal, to within the optical magnification, to the area of tissue corresponding to the elementary microsurface studied.

The optical magnification provided by the intermediate optical devices between this diode 12 and the observed tissue is calculated so that the entire microsurface studied is illuminated by the diode 12 at the same time.

The interferometric configuration is therefore suitable for forming interference patterns in the light coming simultaneously from an entire portion of the eye (or from another body or article) so that an image of this portion is formed by this overall interference pattern, this portion here being an isoplanar surface.

The image measurement device comprises a matrix of amplified or cooled receivers, which make it possible to deliver a matrix electronic image of the tissue scanned.

The interference patterns formed by the interaction between the reference arm and the measurement arm are detected by the matrix sensor 710 and then processed by an electronic and data processing unit 42 in order to extract the signal and display the tissue image.

Within the context of this embodiment of the invention, the isoplanar microsurfaces are scanned in succession by the scanning device 400 and also by virtue of a dynamic mask 720 placed in front of the matrix sensor.

The dynamic mask device 720 consists of a diaphragm spatially scanning the plane detector so as to cover in succession the entire surface thereof.

In other words, the dynamic filtering device 720 exposes that region of the matrix detector 710 corresponding to the microsurface studied to within the magnification and locates it thereon. The dynamic filtering device 720 and the matrix detector 710 are placed in an optical plane conjugate with the tissue plane studied.

By successive transparent-configuration switching of electro-optic filtering elements, a mask is formed which corresponds to the tissue scanning surface, to within the optical magnification. This moving mask scans, stepwise, the plane of the matrix intended to form the image from the set of microsurfaces. The changes in position of the aperture are synchronized and homothetic with the stepping movements of the scanning device 400.

The homothetic and synchronous movement of the position of the microsurface over the photodetecting matrix 710 is provided by the second face of the galvanometer mirror 400.

With a 633 nm source, the resolution obtained with this device is 2 µm in XY and 10 µm in Z.

The use of a mean wavelength of around 488 nm this makes it possible to obtain resolutions of the order of one micrometer in X, Y and a few micrometers in Z for retinal scanning.

In this device, as in the case of the previous device, the compensation means apply a correction to a set of rays coming from a set of points on a chosen surface, these rays having the same wavefront distortion as a calculation point with this correction.

In the present case, the rays coming from these points are sampled simultaneously so that they constitute an overall flux.

The extent of the sampling surface is chosen so that the measured correction at the calculation point is valid for this entire surface.

The backscattered light here is sampled simultaneously over the entire isoplanar surface. Optimal benefit is therefore drawn from each new configuration of the correction mirror 22 by sampling the light over an entire surface, the extent of this surface being chosen so that the compensation is valid over this entire surface. In order for the point of compensation calculation to be properly located in the isoplanar sampling sampling surface, the superluminescent diode 11 emits, in a wavefront distortion measurement phase, a flux which travels a portion of the path which is common with the path of the illumination and backscattering flux.

In the example described here, the extent of the microsurfaces is predetermined by the relative arrangement of the various elements of the device. However, the device may be provided with a module for automatically determining the extent of the surfaces, this module being capable of automatically ensuring their isoplanarity.

In the present setup, the compensation calculation means (that is to say especially the calculation module 21 and the mirror 400 which determines the calculation point) and the image sampling means (that is to say the interferometric means 11, SM1 and the mirror 400, are synchronized so that at each new sampled region, a compensation calculation suitable for this region is carried out.

The setups according to the invention described above make it possible to compensate for any ametropia in the subject. Ametropia compensation is carried out by jointly moving the source device and confocal filtering, for the confocal scanning system, i.e. by moving the reference plane in the case of the interferometric device.

These various apparatuses can be used for observing the cornea, the lens and the fundus of the eye in real time. The arrangements described above make it possible in particular to produce a three-dimensional biomicroscope or ophthalmoscope having a resolution of the order of one micrometer.

Another advantage of the invention is that the chosen device allows operation with a wide illumination pupil, that is to say without the necessity of placing the subject under strict Maxwellian viewing conditions.

The invention substantially improves, by a factor of about 10, the resolution in the three directions in space, while allowing extensive fields to be scanned.

These devices operate for any wavelength for which the eye's optical system is transparent.

However, the devices described above, which make use of a confocal scanning technique or an interferometric technique, are not limited to observing the eye or living bodies; advantageously, they are applied to the observation of manufactured articles, such as semiconductors for example.

Nor is the invention limited to the embodiments described above.

In particular, provision is made according to the invention to combine the three techniques, namely adaptive optics, optical scanning and interferometry.

The optical setup does not necessarily use the principle of separating the illumination and observation pupils, which in this case are superimposed or merged and have the diameter of the subject's pupil.

Under these conditions, the optical beam angle that can be used is wider, thus reducing the diameter of the diffraction spot. Reducing the diffraction spot further increases the resolution.

This makes it possible to use a wider optical pupil than that of the conventional apparatuses, which in this case may be from 7 mm to 9 mm in a normal mydriatic subject. This arrangement further improves the very good resolution of the image.

What is claimed is:

1. A device for observing a body, especially an eye, comprising means (12) for illuminating the body (5), means (400, 450, 500, 700) for sampling the light coming from an illuminated region (01) of the body (5) and compensation means (20) capable of measuring a wavefront distortion of a beam coming from a point on the body (5) and in applying, to the light sampled by the sampling means (400, 450, 500, 700), a correction calculated from this measured distortion, characterized in that the sampling means and the compensation means are arranged so that, for each point on the body used for a correction calculation, the sampling means sample the light over a chosen region of the body sufficiently close to said point of calculation for the wavefront distortion of the light coming from any point in this region is the same as that coming from the point of calculation to within a fraction of a wavelength, and in that the device includes means (400, 450, 500, 700) for automatically changing the point on the body (5) used for the correction calculation and for changing, synchronously, the associated sampling region in such a way that the device scans the observed body in the form of a series of such successive regions for each of which the distortion of the wavefront emanating from any point in the region is identical, to within a fraction of a wavelength, to the distortion of a wavefront emanating from an associated point of calculation.

2. The device as claimed in claim 1, characterized in that the sampling means (400, 450, 500, 700) comprise means (12, SM1) for forming an image of the sampling region by interferometry.

3. The device as claimed in claim 2, characterized in that it comprises a module (12, SM3, SM1, SM4) capable of forming an image by interferometry on the sampled and corrected light.

4. The device as claimed in the preceding claim or claim 2, characterized in that the interferometric means (12, SM1, SM3) form an image of at least one portion of the body (5) not reduced to a point by interferometry simultaneously on the light coming from all of this portion.

5. The device as claimed in one of claim 2, 3 or 4, characterized in that the wavefront compensation is applied to the sampled beam before interference of this beam with a reference beam.

6. The device as claimed in one of claim 3, 4 or 5, characterized in that it comprises a matrix sensor and a modifiable mask synchronized to the sampling means in order to expose, at any moment, an area of the matrix sensor corresponding to the sampling region in question.

7. The device as claimed in claim 6, characterized in that the modifiable mask consists of a set of elements capable of being switched into a transparent position or into an opaque configuration.

8. The device as claimed in claim 1, characterized in that it comprises means (400, 450, 500) for producing, in the sampling region, a point at which the illuminating light rays are concentrated and means (400, 450, 500) for sampling only the direct light rays between the concentration point and an optical entrance (500) of the sampling means.

9. The device as claimed in claim 8, characterized in that provision is made for the concentration point to be scanned over the sampling region.

10. The device as claimed in either of claim 8 or 9, characterized in that it comprises a first deviation module (450) capable of scanning the concentration point in the sampling region and a second deviation module (400) capable of changing the position of the sampling region.

11. The device as claimed in one of claim 8, 9 or 10, characterized in that it includes a photometric sensor (700) capable of converting the sampled light into a signal for controlling an image presentation device and in that the wavefront distortion measurement means (21) and the wavefront correction means (22) are placed in the path of the light between the body and the sensor (700).

12. The device as claimed in claim 11 in combination with claim 8, characterized in that the wavefront distortion correction means (21) are placed between the sensor (700) and the deviation modules (400, 450).

13. The device as claimed in one of claim 8, 9, 10, 11 or 12, characterized in that it comprises a filtering device placed in a plane conjugate with the sampling region, comprising a filtering hole with the diameter of a diffraction spot.

14. The device as claimed in one of the preceding claims, characterized in that the sampling region (01) is chosen to be sufficiently close to the compensation calculation point in question so that the wavefronts coming from any point in this region (01) are identical to within one quarter of a wavelength.

* * * * *